United States Patent [19]

Casley-Smith

[11] Patent Number: 4,616,033
[45] Date of Patent: Oct. 7, 1986

[54] 7 HYDROXY-COUMARIN AS A TREATMENT FOR HIGH PROTEIN OEDEMAS

[75] Inventor: John R. Casley-Smith, Tennyson, Australia

[73] Assignee: Lamorna Investments Proprietary Ltd., Malvern, Australia

[21] Appl. No.: 711,651

[22] Filed: Mar. 14, 1985

[51] Int. Cl.⁴ .............................................. A61K 31/35
[52] U.S. Cl. ..................................................... 514/457
[58] Field of Search ......................................... 514/457

[56] References Cited

PUBLICATIONS

Chem. Abst. 98-27328y, (1983).

*Primary Examiner*—Stanley J. Friedman
*Attorney, Agent, or Firm*—Oldham, Oldham & Weber Co.

[57] ABSTRACT

A method of treating high-protein oedemas in humans or animals by administering the compound 7 hydroxy-coumarin.

5 Claims, No Drawings

7 HYDROXY-COUMARIN AS A TREATMENT FOR HIGH PROTEIN OEDEMAS

This invention relates to the use of 7 hydroxy-coumarin in the treatment of high-protein oedema.

BACKGROUND OF THE INVENTION

Oedema is an abnormal accumulation of fluid in the tissue spaces or cavities of the body. There are five main factors in the formation of generalised oedema and a sixth which plays an important role in the formation of local oedema.

There are:
1. Permability of the capillary wall,
2. & 3. Colliodal osmotic presure of the plasma proteins in the blood and tissues.
4. & 5. Hydro-static pressures in the capillaries and tissues, and
6. Lymphatic obstruction Thus oedema is an unusual swelling of the tissue due to an excessive amount of fluid and can be the result of various causes. Thus haematoma, or in other words a bruise, is one of the most common oedemas. The causes of oedema fall naturally into four groups corresponding to the four classes of oedema, thus 1. High-flow low-protein
2. High-flow high-protein,
3. Low flow high protein, as well as a fourth group of causes of oedema "safety valve insufficiency" which occurs when lymphostasis is superimposed on what would normally be a high flow oedema produced either by excess blood vascular leakage, or the obstruction of a duct of an organ (kidney, pancreas, etc.) the results of which are particularly disastrous for the tissues.

High-protein oedemas are very common in all communities. It has been found that one person in three seeks medical attention every year, in south Australia, for a condition associated with one. The W.H.O. estimates that 250,000,000 people suffer from lymphoedema and elephantiasis, while 250,000 women in Australia suffer from lymphoedema of the arm, of varying grades of severity, after mastectomy. It is highly probable that the improvement produced by the benzo-pyrone group of drugs, in so many different diseases is because they have high-protein oedema associated with them. This always causes reduced oxygenation and function of the tissues. If the oedema is reduced, oxygenation and function are improved. While these drugs do not affect the basic diseases the reduction they produce in associated oedemas improve the function of the tissues and thus the normal healing processes proceed more expeditiously. Examples of this are: lymphoedema, accidental and surgical trauma, haematomas, pancreatitis, heptitis and cirrhosis.

BRIEF STATEMENT OF THE INVENTION

It has been found that the group of Benzo-Pyrones are highly beneficial in the treatment of oedemas, particularly high protein oedemas.

It has been shown that these drugs can effectively reduce high protein oedemas and they do this by increasing the normal proteolysis of the tissues and (to some extent) by increasing lymphatic function. They are thus effective in all diseases which have high protein oedema as part of their disorders. While they do not cure any underlying disease, the fact that they reduce the associated high protein oedema means that they relieve much pain and loss of function. In addition all oedemas cause lowered oxygenation and much harm to the tissues. The high protein ones in particular (if prolonged) cause chronic inflammation and thus their removal is of considerable benefit.

DESCRIPTION OF THE PREFERRED EMBODIMENTS

The benzo-pyrones are a group of compounds which include a number of sub-groups. They contain the flavonoids and their derivates, coumarin and its derivates and a variety of other groups.

The compound, 7 hydroxy-coumarin, is one of the benzo-pyrone group. It shares all their normal properities. Its particular advantage is that it is the principal metabolic product, in man and some animals, of one of the most important members of this group: coumarin. While coumarin has a very low toxicity in man, it is moderately toxic in dogs, rats and some other species—because these do not use the 7 hydroxy-coumarin metabolic route. This compound, 7 hydroxy-coumarin, has a very low toxicity in all these species, yet retains the potency of coumarin in high-protein oedema.

It has been found that the benzo-pyrones as noted above are very effective in the treatment of high protein oedemas. It has been found that the use of the benzo-pyrone affects the oedema in four ways 1. Excessive protein loss from the blood vessels can be reduced,
2. Protein and fluid removal by the lymphatics can (under certain conditions) be increased.
3. More phagocytosis of protein by cells in the tissues occurs, and
4. The intracellular or extracellular, lysis of proteins by cells in the tissues are made greater.

It should be realized however that it may be rare for a benzo-pyrone to have only one action in a particular disease; similarly, it is rare for a particular disease to have only one cause or to derange only one of the body's functions. Thus for example a burn gives a high protein oedema because of the injured blood vessels, but frequently the collecting lymphatics go into spasm producing a super-imposed lymphoedema, i.e. there is a 'safety valve' insufficiency; treating a burn with a benzo-pyrone may well affect the open blood capillary endothelial junctions, interfere with the mediators of inflammation, alter the permeability of the interstitial tissue, increase the extravascular proteolysis and cause the collecting lymphatics to pump more lymph.

Benzo-pyrones, while often opening blood vasculor junctions, can greatly reduce blood vascular endothelial damage in certain circumstances. These include preventing the opening of the post capillary venular endothelial junctions, preventing endothelial cells leaving the vessel wall with a consequent huge gap in its lining, and acting as vitamin-P substances when the patient is deficient in this.

It has been shown that benzo-pyrones can increase the pumping capacity of the collecting lymphatics and that they also cause an increased production of urine.

Increased phagocytosis may indeed occur, but the phagocytosed macromolecules are not retained in the tissues. In burns the removal of the protein was considerably increased by coumarin under all conditions. The removal non-metabolisable tracer PVP, was slowed by the coumarin in the normal and burnt legs-possibly because phagocytosis was enhanced (with the non-metabolisable PVP being retained in the phogocytes); the PVP was however more rapidly removed with coumarin in the presence of lymphodema—probably because the reduction of oedema reduced the distances it had to travel to reach blood capillaries. The important thing is that the protein removal from the limbs was much more rapid with courmarin. This shows that it is not simply phagocytosed and retained in the phagocytes in the region.

It has also been shown by exclusion that, when the benzo-pyrones reduce high protein oedemas they must increase proteolysis and secondly it was found that the ratios of radio-labelled-protein-fragments, to the labelled protein, increased greatly when treated with coumarin, thirdly that the benzo-pyrones have been shown to induce increased levals of proteases in the oedema fluid, in the whole tissues, and in the plasma and lymph, and fourthly they increase proteolysis by macrophages in vitro,—fifthly they lose their ability to reduce high protein oedemas when the macrophages are selectively poisoned.

Thus it can be seen that the use of benzo-pyrones, particularly coumarin is particularly effective in reducing all forms of oedema, and the dosage and treatment will vary according to the particular oedema being treated.

The compound 7 hydroxy-coumarin is used in the treatment of all forms of high-protein oedema (i.e. of oedema with a protein content of more than 0.5 g/dl) associated with any disease, in man or animals, including: lymphoedema and elephatiasis—including protein-losing enteropathies and other forms of lymph reflux, and transplantation oedema, also some forms of pseudotumour cerebri (lymphostatic encephalopathy) ascites, pleural and pericardial effusions, pulmonary congestion—including asthma of allergic or traumatic origin, all forms of excessive fibrosis—including that of chronic tuberculosis, the varicose vein syndrome and chronic venous insufficiency, peripheral artieral insufficiency and the post-ischaemic syndrome, accidental and surgical trauma—including burns (heat, cold, or chemical), and cerebral and ocular oedema, acute and chronic inflammation of general—including infections, rheumatoid arthritis and all forms of auto-immune diseases, hepatitus of any cause, hepatic cirrhosis, acute and chronic pancreatitis, diabetic retinopathy metabolic disorders and vitamin dificiencies, and psychiatric disorders—in particular, schizophrenia.

The compound can be used to reduce hypercholesterolaemia and hyperlipidaemia, as antihelminthics, and to improve postrual hypotension. Also the treatment of cerebral oedema from any cause, including trauma, infection, degeneration, haemorrhage, thrombosis and demyelinating diseases, including multiple sclerosis, hyphaema, endocrine and other ophthalmopathies involving oedema, Meniere's Disease, aphthous ulcers, ulcers from any other cause, haemorrhoids and their complications, ascites, and effusions in other body cavities, including joints, complications caused by intrauterine devices, hepatic toxicity caused by various poisons, including drugs, inflammation caused by ionising radiations and ultra-violet rays, pancreatitis from any cause, fragility of the blood vessels and migraine.

Additionally, for the treatment of venous thrombosis and embolism, including that of the central retinal vein and other conditions involving agglutination of platelets or erythrocytes, conditions in which the lymphatic system is inadequate for its load, habitual abortion, neoplasia and other conditions in which immune function is depressed, or which can be treated by increasing this.

It is to be noted that some benzo-pyrones kill bacteria, viruses, intestinal parasites, and those which do not, at least do not worsen the conditions (e.g. during infection)—unlike the action of steroids.

Benzo-pyrones have anti-neoplastic activity and may be used to control or destroy, neoplasms (including carcinoma and melanomas).

The compounds can be used in allergic conditions—of the skin, mucosa, and deeper organs (autoimmune diseases), and used in diabetic retinopathy, cataract, and other diabetic manefestations of increased blood vascular permeability, and also to improve the functioning of the lymphatic system.

The amount of dead heart muscle can be reduced by use of the compound, and disorders of the initiation and conduction of the contraction of the heart, in myocardial infarction and other heart conditions involving oedema.

Fevers, pain and the desquamation of endothelial cells can be reduced, and used in crytogenic fibrosing alveolitis and to prevent the agglutination of erythocytes and platelets.

It is to be noted that this is only a short list of the conditions associated with high-protein oedemas. Any high-protein oedema is deleterious, and that although it may not be a major part of some disease, it should always be treated if possible.

The compound is to enhance the function of macrophages, neutrophils and other cells concerned with the immune and phagocytic systems, particularly in order to increase their destruction of neoplasms, but also to increase their proteolytic and other functions; and to stabilise plasma and lysosomal membranes, to decrease erythrocyte and platelet aggregation, to normalise prostaglandin production and function, and to relax smooth muscles.

In one example there is produced a cream comprising between 2.5% and 90% by weight of 7 hydroxy-coumarin in an inert cream base, such as cetomacrosol, the prepared proportion being 20% by weight for administration to the skin or mucous membranes.

The modes of administration can include: orally, rectally and vaginally; administration by injection, or other methods (e.g. direct surgical placement, iontophoresis) into any parts of the body, including: intravenous, cutaneous, subcutaneous, intramuscular, intraperitonel injection, application to the skin or mucous membranes, whether incorporated in a cream, powder, ointment, paste (including tooth paste), spray, lotion, or in any other manner. It may be administered either alone, or associated with other compounds with similar actions or complementary ones.

I claim:

1. A method of treating high-protein oedemas in a human or animal in need of such treatment which comprises administering to said human or animal a pharmaceutically effective amount of the compound 7 hydroxy-coumarin.

2. The method as defined in claim 1 characterised in that the compound is administered internally, either orally, rectally, vaginally, by injection or surgical placement.

3. the method as defined in claim 1 characterised in that the compound is administered to the skin or mucous membranes by incorporation in cream, powder, ointment, paste, spray or lotion.

4. A method according to claim 3 wherein said compound is incorporated in a cream.

5. A method according to claim 4 wherein said cream contains from 2.5 percent to 90 percent by weight of said 7-Hydroxy-Coumarin.

* * * * *